(12) United States Patent
Schulze et al.

(10) Patent No.: US 9,272,976 B2
(45) Date of Patent: Mar. 1, 2016

(54) METHOD FOR PURIFYING CARBOXYLIC ACIDS FROM FERMENTATION BROTHS

(71) Applicants: Joachim Schulze, Soest (DE); Wolfgang Tietz, Biendorf (DE); Isabel Waengler, Berlin (DE); Klaus Kuehlein, Kelkheim (DE)

(72) Inventors: Joachim Schulze, Soest (DE); Wolfgang Tietz, Biendorf (DE); Isabel Waengler, Berlin (DE); Klaus Kuehlein, Kelkheim (DE)

(73) Assignee: THYSSENKRUPP INDUSTRIAL SOLUTIONS AG, Essen (DE)

( * ) Notice: Subject to any disclaimer, the term of this patent is extended or adjusted under 35 U.S.C. 154(b) by 0 days.

(21) Appl. No.: 14/363,844

(22) PCT Filed: Nov. 15, 2012

(86) PCT No.: PCT/EP2012/004741
§ 371 (c)(1),
(2) Date: Jun. 9, 2014

(87) PCT Pub. No.: WO2013/083229
PCT Pub. Date: Jun. 13, 2013

(65) Prior Publication Data
US 2014/0371486 A1      Dec. 18, 2014

(30) Foreign Application Priority Data
Dec. 9, 2011   (DE) .......................... 10 2011 120 632

(51) Int. Cl.
*C07C 51/42*   (2006.01)
*C07C 51/47*   (2006.01)
*B01D 61/08*   (2006.01)

(52) U.S. Cl.
CPC ............. *C07C 51/47* (2013.01); *B01D 61/08* (2013.01); *C07C 51/42* (2013.01)

(58) Field of Classification Search
None
See application file for complete search history.

(56) References Cited

U.S. PATENT DOCUMENTS

| | | | |
|---|---|---|---|
| 4,323,702 A | 4/1982 | Kawabata et al. | |
| 5,034,105 A | 7/1991 | Berglund et al. | |
| 5,143,834 A | 9/1992 | Glassner et al. | |
| 5,168,055 A | 12/1992 | Datta et al. | |
| 5,681,728 A * | 10/1997 | Miao .......................... | 435/136 |
| 6,137,004 A | 10/2000 | McQuigg | |
| 6,291,708 B1 | 9/2001 | Cockrem | |
| 6,489,508 B1 | 12/2002 | Van Gansbeghe et al. | |
| 2002/0004611 A1 | 1/2002 | Eyal et al. | |
| 2009/0162892 A1 | 6/2009 | Pompejus et al. | |
| 2010/0273224 A1 | 10/2010 | Joachim et al. | |

FOREIGN PATENT DOCUMENTS

| | | |
|---|---|---|
| DE | 1274128 | 8/1968 |
| DE | 3043766 A1 | 6/1981 |
| DE | 69006555 T2 | 8/1994 |
| DE | 69015019 T2 | 7/1995 |
| DE | 69015233 T2 | 8/1995 |
| DE | 19939630 C2 | 3/2001 |
| DE | 69815369 T2 | 5/2004 |
| DE | 69821951 T2 | 12/2004 |
| DE | 102004026152 A1 | 12/2005 |
| DE | 60028958 T2 | 2/2007 |
| DE | 102007045701 B3 | 5/2009 |
| DE | 102009019248 A1 | 11/2010 |
| EP | 0135728 A1 | 4/1985 |
| EP | 0986532 B2 | 10/2006 |
| GB | 1129125 A | 10/1968 |
| WO | 93/06226 A1 | 4/1993 |
| WO | 96/41021 A1 | 12/1996 |
| WO | 9909196 A1 | 2/1999 |
| WO | 9919290 | 4/1999 |
| WO | 2006/124633 A1 | 11/2006 |
| WO | 2011/082378 A2 | 7/2011 |

OTHER PUBLICATIONS

German Language International Search Report for International Patent Application No. PCT/EP2012/004741; Mailing date Feb. 26, 2013.
English Translation of International Search Report for International Patent Application No. PCT/EP2012/004741; Mailing date Feb. 26, 2013.
J. Dahlmann et al., British Polymer Journal, vol. 23 (1990), pp. 235-240.
English Translation of the International Preliminary Report on Patentability including the corresponding Written Opinion of the International Searching Authority for International Application No. PCT/EP2012/004741, mailing date Jun. 19, 2014.
English translation of abstract of DE 102009019248 A1.
English translation of abstract of EP 0135728 A1.
English translation of abstract of EP counterpart (EP19939630 A1) to German patent No. DE19939630 A1. (Note: no English abstract of German pat. No. DE19939630 A1 was available, and no English language counterpart patent or application is available).

* cited by examiner

*Primary Examiner* — Yevegeny Valenrod
(74) *Attorney, Agent, or Firm* — ThyssenKrupp North America, Inc.

(57) ABSTRACT

Disclosed is a method for removing and purifying carboxylic acids from fermentation broths, comprising removing biomass and any solids present from the fermentation broth, finely cleaning up the biomass-free and solids-free fermentation broth by nanofiltration, and removing the carboxylic acid from the finely cleaned, biomass-free, and solids free fermentation broth by adsorption to one or more solid phases having tertiary amino groups.

17 Claims, 1 Drawing Sheet

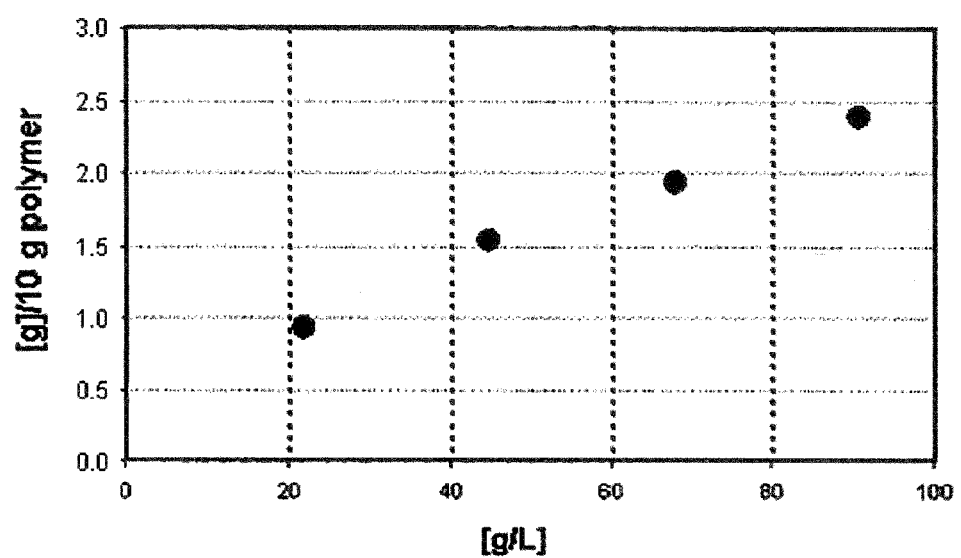

METHOD FOR PURIFYING CARBOXYLIC ACIDS FROM FERMENTATION BROTHS

CROSS REFERENCE TO RELATED APPLICATIONS

This application is a U.S. National Stage Entry of, and claims priority to, International Patent Application Serial Number PCT/EP2012/004741, filed Nov. 15, 2012.

FIELD

The invention relates to a method for purifying carboxylic acids from fermentation broths, and to a device for carrying out the method according to the invention. The isolation of carboxylic acids which cannot be removed by distillation or can only be removed with difficulty by distillation is very complex.

BACKGROUND

Critical to the industrial use of carboxylic acids which are generated by fermentation of carbohydrate-containing substrates using various microorganisms is the cost-effectiveness and efficiency of removing and cleaning up the lactic acid from these aqueous fermentation solutions, which contain not only the carboxylic acid or the carboxylic acid salts but also further organic acids, other fermentation byproducts, microorganisms and the constituents thereof and also remnants of the substrates, such as sugars. These impurities interfere with the subsequent further processing of the carboxylic acids generated. For example, lactic acid is polymerized to form polylactic acid in order to produce biogradable plastics. For this purpose, it is necessary to use extremely pure monomer in order to achieve a high degree of polymerization of the lactic acid. This has been known for a long time and is disclosed by, for example, J. Dahlmann et al., British Polymer Journal, vol. 23 (1990), pp. 235-240.

A similar situation is known to exist for succinic acid for example. The grades of the succinic acid generated can be differentiated by subdivision into a technical grade having a succinic acid content of at least 97% by mass and a succinic acid which is especially suitable for use for polymerization (polymer grade or 1,4-butanediol grade) and has a content of at least 99.5% by mass.

A multiplicity of patents provide a description of obtaining succinic acid from fermentation solutions, including
- extractive processes using extraction agents such as tributylamines, trialkylamines, olefins, various alcohols and aromatic hydrocarbons,
- processes using calcium hydroxide and sulfuric acid, producing gypsum as byproduct,
- processes using electrodialysis,
- thermal methods such as fractional distillation or thermally graduated chromatography,
- high-pressure extraction using $CO_2$,
- membrane methods such as, for example, reverse osmosis and other filtration processes and these patents also discuss interlinkings of these methods and modification by further steps corresponding to the prior art. Such methods are described, inter alia, in patent documents DE 69821951 T2; DE 69015233 T2; DE 69015019 T2; DE 69006555 T2; DE 69015019; DE 60028958T2; DE 10 2004 026152 A1.

In addition, a multiplicity of methods concerning the purification of lactic acid are known.

For example, some patents teach the use of distillation to purify lactic acid from aqueous solutions. EP 0986532 B2 takes advantage of such a method. DE 10 2007 045 701 B3 discloses combined extraction with linear n-trioctylamine (TOA) and distillation. Further possibilities known in the literature are electrodialysis or esterification with an alcohol, with distillation and then hydrolysis of the ester formed likewise being carried out thereafter. These methods are extremely cost-intensive. Moreover, distillation has the disadvantage that a portion of the carbohydrates is also always coextracted, leading to a deterioration of the yield of the entire process and impeding the isolation of the product.

Processes using calcium hydroxide and sulfuric acid, with gypsum being produced in large quantities as byproduct, are also known. In this connection, it was additionally found that lactic acid can be isolated using chromatographic methods from, for example, a sulfuric acid-acidified fermentation broth containing not only free lactic acid but also ammonium and sulfate ions. For example, DE 69815369 T2 describes, inter alia, the removal of lactic acid from aqueous mixtures by adsorption to a solid adsorbent; in this case, preference is given to using a solids adsorbent which adsorbs lactic acid as opposed to lactate. More particularly, according to the above document, weak anion exchangers are a possibility for the isolation of lactic acid. DE 10 2009 019 248 A1 further describes chromatographic methods for purifying organic acids, in particular lactic acid, by carrying out simulated moving bed chromatography.

WO 2006/124633 A1 describes a process for producing ammonium lactate by fermentation. During the fermentation, the ammonium salt of lactic acid is formed, which salt can be removed from the fermentation solution by, for example, extraction. In a subsequent step, the ammonium salt can be split very easily using weak acids or carbon dioxide. In said step, the free lactic acid is obtained, which can then be cleaned up by, for example, distillation.

WO99/19290 describes fermentation of lactic acid with subsequent filtration and extraction, it being possible for the extraction to be an adsorption. This document does not disclose the nature of the interaction with the adsorption solid phase. A similar method is disclosed in WO93/06226, the adsorption solid phase in this case being provided with tertiary amino groups and the rate of production of free acid being increased as a result. EP0135728 also teaches the isolation of enzymatically generated carboxylic acids via adsorbers provided with tertiary amino groups. In this case, the fermentation takes place via column-immobilized cells.

A disadvantage of many methods is that additional substances are supplied to the process, which substances must no longer be present in the target product or the traces of which substances in the target product may lead to limitations in the quality and the applicability of the product. The practical implementation of the methods is also associated in some cases with considerable technical complexity and considerable energy consumption.

For instance, DE19939630C2 discloses a method for finely cleaning up aqueous solutions containing organic acid produced by fermentation, such as, for example, citric acid, lactic acid, succinic acid or tartaric acid. In said method, the solution coming from the fermentation is first filtered and the resulting solution is subsequently delivered across an anion exchanger and a subsequent adsorber resin bed. The adsorber resin bed used for the fine cleanup is initially loaded with $OH^-$ ions and binds the product acid. Moreover, further purification of the filtered solution, downstream of the filtration, in order to remove impurities present such as, for example, cell debris, carbohydrates, nutrients, amino acids and sugars is not mentioned.

DE69815369T2 describes the isolation of lactic acid from a fermentation broth by adsorption of the lactic acid to a solid adsorbent with subsequent generation of the lactic acid from the solid adsorbent, with removal of the biomass taking place beforehand by filtration. In this case, the solid adsorbent can be a poly-4-vinylpyridine resin or a tertiary polystyrene divinylbenzene amine resin. An intermediate step for removing further impurities is not taught here either.

BRIEF DESCRIPTION OF THE DRAWING

The present disclosure is described in detail below with reference to the attached drawing FIGURE, wherein:

FIG. 1 is an exemplary graph depicting the resulting lactic acid loading capacity of polymer adsorber resin, in grams of lactic acid adsorbed by 10 grams of polymer versus the concentration, in grams per liter, of the lactic acid solution that is passed through the polymer resin, after pre-concentration of lactic acid, in an exemplary embodiment of a method as disclosed herein.

DETAILED DESCRIPTION

It is an object of the invention to provide a method for removing and purifying carboxylic acids from fermentation broths, which method exhibits a high product purity of ≥80% by mass and avoids known disadvantages of other methods.

The invention achieves the object by using a method for removing and purifying carboxylic acids from fermentation broths, wherein the method comprises the following steps,
a. removing the biomass and any solids present from the fermentation broth,
b. finely cleaning up the fermentation broth from method step a) by nanofiltration,
c. removing the carboxylic acid by adsorption to one or more solid phases having tertiary amino groups.

The advantage of said method is that the fine cleanup arranged before the adsorption greatly reduces the impurities content in the fermentation broth from method step a), which broth is subsequently delivered across the adsorption solid phase, making it possible to further increase the rate of production of carboxylic acid and reducing expenditure in terms of apparatus, creating a method less expensive than that disclosed in EP0135728 for example. Fermentation broths contain not only the desired carboxylic acid but also cell debris, carbohydrates, nutrients and further impurities, such as, for example, amino acids and sugars. In the case of highly impure fermentation solutions, EP0135728 proposes adsorbing the carboxylic acids only to some extent and carrying out a recirculation method, this being very complex.

A further advantage of the method according to the invention is that there is no neutralization during the fermentation and that the removal and purification take place with the free acid and not with the salt thereof, as is frequently the case in the prior art. Thus, the method is simplified in that absolutely no acidification step is required and thus, also, there are absolutely no further substances added during the fermentation which need to be removed, which substances are normally used for neutralization in the prior art.

For the fermentation itself, it is possible to use a multiplicity of microorganisms, including bacteria, yeasts and fungi. The fermentation broth may also contain various recycling streams from the overall method.

The fermentation broth containing the carboxylic acid, biomass and constituents of the substrate is continuously supplied for precoat filtration and/or microfiltration and/or ultrafiltration. The resulting removed biomass is optionally recycled to the fermenter again. During the biomass removal step in method step a), the temperature and pH match the fermentation values, since it has been found that autolysis of the biomass is sped up and more lysis products are released into the fermentation broth as a result of inactivation of the biomass by raising the temperature and lowering the pH by addition of acid. Also, the time between ending the fermentation and the removal of the biomass should be kept as short as possible and should be no more than 2 h, and be preferably less than 1-2 h. The biomass concentration in the filtrate should not exceed 1 g/l. This process control has a positive influence on the quality of the end product.

In order to generate the production of carboxylic acids in a high-purity grade, fine cleanup, which preferably takes the form of nanofiltration, is carried out in method step b) because remnants of dyes and of accompanying substances are still present. In said step, membranes having a separation factor of from 100 to 400 Da are used. It was possible to demonstrate that nanofiltration using a separation factor of 200 Da yields good quality results. In said nanofiltration, the process is conducted in such a way that the nanofiltration retentate is not more than 10% of the total throughput. The permeate is supplied to additional method step c).

In an advantageous embodiment of the method according to the invention, reverse osmosis is carried out between method steps b) and c). This step is understood to be an exemplary additional option for concentration before the adsorption. Other modes of concentration using methods known from the prior art or a combination of said known methods are encompassed by the disclosure content of the present invention.

In method step c), preference is given to using tertiary amino groups which are pyridine groups, which are preferably selected from the group comprising polyvinylpyridine and poly-2- or poly-4-vinylpyridines. Particular preferably, the one or more solid phases used in method step c) for adsorption is a polymer crosslinked with divinylbenzene. In this case, the one or more solid phases used in method step c) for adsorption is formed from one or more different polymer materials. Further suitable polymers having tertiary amino groups which selectively adsorb carboxylic acids and allow the desorption thereof using polar solvents are described in, for example, DE 1274128 and DE 3043766.

In method step c), the adsorbed carboxylic acids are preferably desorbed by treatment with a polar solvent from the group consisting of the aliphatic alcohols, aliphatic ketones and aliphatic carboxylic esters. Particularly preferably, the desorption is achieved using methyl acetate or ethyl acetate, acetone or methyl ethyl ketone and, in particular, using low-molecular-weight alcohols such as ethanol and, especially advantageously, using methanol. Another possibility is desorption using water, which is advantageously heated to a temperature of from 20° C. to 60° C.

The solvent is optionally subsequently removed from the carboxylic acid by means of distillation and/or the product is crystallized. In addition, further cleanup steps, such as activated carbon filtration and/or anion and/or cation exchange, can be provided after the desorption from the adsorption solid phase.

Preferably, the carboxylic acid to be removed and to be purified is selected from the group comprising hydroxycarboxylic acids and dicarboxylic acids. In this case, the hydroxycarboxylic acid is selected from the group comprising malic acid, glycolic acid, isocitric acid, mandelic acid, lactic acid, tartronic acid, tartaric acid, citric acid, β-hydroxybutyric acid, mevalonic acid and salicylic acid, and is preferably lactic acid.

In a further embodiment of the invention, the dicarboxylic acid is selected from the group comprising oxalic acid, maleic acid, succinic acid, glutaric acid, adipic acid, pimelic acid, suberic acid, fumaric acid and itaconic acid, and is preferably succinic acid.

Furthermore, the present invention claims a device for carrying out the method outlined in claim 1.

The present invention will now be more particularly elucidated on the basis of four exemplary embodiments.

Exemplary Embodiment 1

A process chain without nanofiltration as fine cleanup is demonstrated:

A fermentation broth containing, by way of example, lactic acid, biomass and constituents of the substrate was continuously separated from the biomass by means of precoat filtration and microfiltration. The resulting broth contained 2% lactic acid. The lactic acid-containing permeate having a 2% content is used in an adsorption-desorption experiment. In said experiment, use is made of an adsorber resin which bears poly-4-vinylpyridines as active component and is crosslinked with divinylbenzene and has been polymerized into a spherical structure. Here, the lactic acid can be considered to be an exemplary representative of a carboxylic acid. By means of the adsorber resin, the lactic acid is bound to the resin from the lactic acid solution. In a subsequent desorption step, the lactic acid is recovered. For the desorption, 40° C. warm water was used here. The results can be found in table 1 below.

TABLE 1

Adsorption and desorption of lactic acid on an amino group-bearing adsorber resin, the desorption having been carried out using water having a temperature of 40° C.:

| Cycle | Absolute lactic acid bound on resin [g] after 5 min | Absolute lactic acid in supernatant [g] after 5 min | Lactic acid desorbed [%] |
| --- | --- | --- | --- |
| 1 | 1.13 | 0.65 | 35 |
| 2 | 0.64 | 0.76 | 85 |
| 3 | 0.56 | 0.65 | 92 |
| 4 | 0.54 | 0.69 | 94 |
| 5 | 0.56 | 0.63 | 92 |
| 6 | 0.38 | 0.67 | 111 |

Table 1 shows a 6-fold adsorption-desorption cycle. 10 g of an adsorber resin were used. It was possible to demonstrate that desorption to an extent of approximately 100% is possible. In summary, it can be stated that the loading capacity is 0.54 g of lactic acid per 10 g of polymer when 40° C. warm water is used for the desorption. The desorption in % is 95%, calculated across the last 5 cycles. The first loading/unloading cycle shows a higher adsorption of 1.13 g of lactic acid and a reduced desorption. This can be explained by the fact that the resin initially needs to be charged with a base load.

The product thus obtained still has the following impurities:
100% discoloration of the broth
100% glucose
100% maltose and other disaccharides and higher saccharides
100% proteins
100% peptides
100% amino acids
100% sulfates
100% ammonium salts
100% lactic acid The impurities still present interfere with subsequent processing of the lactic acid to form, for example, polylactic acid. Thus, in the case of this sequence of process steps, yet further adsorption-desorption cycles are required in order to achieve a correspondingly desired product quality, since the further impurities also partly adsorb to the column material. Thus, a relatively large number of adsorption columns would be required. The impurities adsorbing to the column material partly desorb together with the desired carboxylic acid, and so further purification steps would be required after the adsorption.

Exemplary Embodiment 2

A process chain including nanofiltration as fine cleanup is demonstrated.

A fermentation broth containing carboxylic acids, such as, for example, lactic acid, was generated by fermentation of microorganisms. During said fermentation, the pH was kept constant between 6.0 and 7.3, and no neutralizing agents, such as NaOH, were added while doing so. This was achieved by continuously withdrawing fermentation broth and supplying it for purification. To this end, in the case of an average lactic acid productivity during fermentation of 4 g/l/h and the indicatated pH range, it is necessary to design the following microfiltration of method step a) and the nanofiltration of method step b) in such a way that the volume of the permeate from the nanofiltration corresponds to 2×the operational volume of the fermenter.

The fermentation broth, containing by way of example lactic acid, biomass and constituents of the substrate, was continuously separated from the biomass by means of precoat filtration and microfiltration. The resulting broth contained 2% lactic acid. During the separation, it was made sure that the temperature and the pH correspond to the values for the fermentation carried out. The following fine cleanup was performed as a nanofiltration. For said nanofiltration, a membrane having a separation factor of 200 Da was used. It was made sure that the nanofiltration was carried out at a temperature which corresponded to that for the fermentation, with a temperature difference of ±5° C. being tolerated. In this connection, operations were carried out within a temperature range of from 48° C. to 52° C. The fermentation pH, which varies between 6 and 7.3, was also retained. The fact that the temperature and the pH for the purification steps correspond to the values for the fermentation entails the advantage of a gentle cleanup, leading to less destruction of the lactic acid end product and thus to an increase in yield. During the purification steps, operations were carried out at a pressure of 40 bar, though operations can be carried out within a pressure range of from 10 to 40 bar.

The product thus obtained still has the following impurities:
15-20% discoloration of the broth
72-74% glucose
12-15% maltose and other disaccharides and higher saccharides
20-25% proteins
20-25% peptides
35-42% amino acids
28-32% sulfates
25-50% ammonium salts
95-98% lactic acid It was thereby possible to remove the majority of the impurity from the lactic acid-containing stream in a very gentle manner. The retentate stream, which is produced during the nanofiltration and which contains the impurities, can also be recycled for fermentation again.

The lactic acid-containing permeate having a 2% content was used in an adsorption-desorption experiment. In said experiment, use was made of an adsorber resin which bears poly-4-vinylpyridines as active component and is crosslinked with divinylbenzene and has been polymerized into a spherical structure. Here, the lactic acid can be considered to be an exemplary representative of a carboxylic acid. By means of the adsorber resin, the lactic acid is bound to the resin from the lactic acid solution. In a subsequent desorption step, the lactic acid is recovered. For the desorption, 40° C. warm water was used here. The results can be found in table 1 below.

TABLE 2

Adsorption and desorption of lactic acid on an amino group-bearing adsorber resin, the desorption having been carried out using water having a temperature of 40° C.:

| Cycle | Absolute lactic acid bound on resin [g] after 5 min | Absolute lactic acid in supernatant [g] after 5 min | Lactic acid desorbed [%] |
|---|---|---|---|
| 1 | 1.26 | 0.49 | 39 |
| 2 | 0.71 | 0.61 | 87 |
| 3 | 0.63 | 0.57 | 90 |
| 4 | 0.58 | 0.56 | 97 |
| 5 | 0.64 | 0.55 | 86 |
| 6 | 0.43 | 0.54 | 127 |

Table 1 shows a 6-fold adsorption-desorption cycle. 10 g of an adsorber resin were used. It was possible to demonstrate that desorption to an extent of approximately 100% is possible. In summary, it can be stated that the loading capacity is 0.59 g of lactic acid per 10 g of polymer when 40° C. warm water is used for the desorption. The desorption in % is 97%, calculated across the last 5 cycles. The first loading/unloading cycle shows a higher adsorption of 1.26 g of lactic acid and a reduced desorption. This can be explained by the fact that the resin initially needs to be charged with a base load.

Exemplary Embodiment 3

The biomass removal and fine cleanup was carried out as elucidated in exemplary embodiment 2. Exemplary embodiment 3 differs from exemplary embodiment 2 in the choice of desorption agent. In exemplary embodiment 3, methanol was used as an example of an aliphatic alcohol. The results can be found in table 3 below.

TABLE 3

Adsorption and desorption of lactic acid on an amino group-bearing adsorber resin, with the desorption having been carried out with methanol:

| Cycle | Absolute lactic acid bound on resin [g] after 5 min | Absolute lactic acid in supernatant [g] after 5 min | Lactic acid desorbed [%] |
|---|---|---|---|
| 1 | 1.14 | 0.84 | 73 |
| 2 | 0.85 | 0.92 | 108 |
| 3 | 0.74 | 0.9 | 121 |
| 4 | 0.77 | 0.87 | 113 |
| 5 | 0.76 | 0.84 | 106 |
| 6 | 0.77 | 0.86 | 112 |

Table 3 shows a 6-fold adsorption-desorption cycle. The loading capacity of the adsorber resin is 0.78 g of lactic acid per 10 g of polymer when methanol is used for the desorption. The desorption in % is at least 100%, calculated across the last 5 cycles. Here too, the first loading/unloading cycle shows a higher adsorption of 1.14 g of lactic acid and a reduced desorption. Here too, this can be explained by the fact that the resin initially needs to be charged with a base load.

Thus, the advantages of combining the adsorption to one or more solid phases having tertiary amino groups with fine cleanup performed as a nanofiltration is, above all, that fewer adsorption-desorption cycles are required and thus, also, fewer columns are needed. As a result, the method becomes more cost-effective. Also, the product following the desorption is pure to such an extent that it is directly suited for further processing, for example for producing polylactic acid. A further advantage is the prolongation of the operating life of the resins because of the removal of impurities which permanently damage the resin. Possible components are, inter alia, sugars, dyes and peptides.

Exemplary Embodiment 4

The biomass removal and fine cleanup was carried out as elucidated in exemplary embodiment 2. Exemplary embodiment 4 differs from exemplary embodiment 2 by an additional method step. In exemplary embodiment 4, reverse osmosis (RO) was additionally applied after the NF. The results can be found in FIG. 1.

FIG. 1: Loading capacity after preconcentration of lactic acid

In FIG. 1, the amount of lactic acid in g adsorbed to 10 g of polymer is plotted against the concentration of lactic acid solution in g/L, which was used to load the column. It is clear from this graph that the loading capacity increases with the concentration of lactic acid. Concentration by a factor of 4.5 leads to a 2.5-fold increase in loading. Further concentration by other measures known from the prior art or a combination of said known measures is encompassed by the scope of this application. This effect does not have a negative influence on the desorption of the acid and is comparable with that of exemplary embodiment 2.

As a result of the additional method step, substantially less resin is needed for the adsorption. In addition, the lactic acid concentration after the desorption is higher and the effort required for further concentration is thus less.

The invention claimed is:

1. A method for removing and purifying carboxylic acids from fermentation broths by use of an adsorption material disposed in an adsorption column, comprising:
   removing biomass and any solids present from the fermentation broth;
   nanofiltering the biomass-free and solids-free fermentation broth to remove impurities therefrom and reduce an amount of the impurities that may contact and be adsorbed into the adsorption material in the adsorption column, thereby increasing a rate of production of carboxylic acid; and
   removing the carboxylic acid from the nanofiltered, biomass-free, and solids free fermentation broth by adsorption to one or more solid phases of adsorption material having tertiary amino groups.

2. The method of claim 1, wherein said removing biomass from the fermentation broth is achieved by at least one of precoat filtration, microfiltration, or ultrafiltration.

3. The method of claim 2, further comprising:
recycling the removed biomass back to the fermenter.

4. The method of claim 2, wherein said removing biomass from the fermentation broth is achieved without lowering the pH of the fermentation broth and without thermal inactivation of the biomass.

5. The method of claim 2, wherein during said step of removing biomass and any solids present, an elapsed time between an end of fermentation and the removal of the biomass is no more than 2 hours.

6. The method of claim 2, wherein a biomass concentration in a filtrate from the at least one of precoat filtration, microfiltration, or ultrafiltration is not greater than 1 g/l.

7. The method of claim 1, wherein said nanofiltering step utilizes nanofiltration membranes having a separation cut-off of from about 100 to about 400 Da.

8. The method of claim 1, further comprising:
subjecting the nanofiltered fermentation broth to reverse osmosis.

9. The method of claim 1, wherein the tertiary amino groups are pyridine groups selected from the group consisting of polyvinylpyridine, poly-2-vinylpyridines, and poly-4-vinylpyridines.

10. The method of claim 1, wherein the one or more solid phases of adsorption material used for adsorption is a polymer crosslinked with divinylbenzene.

11. The method of claim 1, wherein the one or more solid phases of adsorption material used for adsorption is formed from one or more different polymer materials.

12. The method of claim 1, wherein the carboxylic acids to be removed and purified are selected from the group consisting of hydroxycarboxylic acids and dicarboxylic acids.

13. The method of claim 12, wherein the hydroxycarboxylic acid is selected from the group consisting of malic acid, glycolic acid, isocitric acid, mandelic acid, lactic acid, tartronic acid, tartaric acid, citric acid, β-hydroxybutyric acid, mevalonic acid and salicylic acid.

14. The method of claim 12, wherein the dicarboxylic acid is selected from the group consisting of oxalic acid, maleic acid, succinic acid, glutaric acid, adipic acid, pimelic acid, suberic acid, fumaric acid and itaconic acid.

15. A device for removing and purifying carboxylic acids from fermentation broths, comprising:
means for removing biomass and any solids present from the fermentation broth;
a nanofiltration device in fluid communication with the means for removing biomass from the fermentation broth, said nanofiltration device being configured to reduce an amount of the impurities that may contact and be adsorbed into the adsorption material in the adsorption column, thereby increasing a rate of production of carboxylic acid; and
means for removing the carboxylic acid from the finely cleaned, biomass-free, and solids free fermentation broth by adsorption to one or more solid phases having tertiary amino groups.

16. The method of claim 1, wherein said nanofiltering step utilizes nanofiltration membranes having a separation cut-off of 200 Da.

17. The method of claim 12, wherein the hydroxycarboxylic acid is lactic acid.

* * * * *